(12) United States Patent
Okada et al.

(10) Patent No.: US 7,150,870 B2
(45) Date of Patent: Dec. 19, 2006

(54) ANTI-TUMOR AGENT

(75) Inventors: Futoshi Okada, Hokkaido (JP); Masuo Hosokawa, Hokkaido (JP); Hiroshi Shionoya, Saitama (JP)

(73) Assignees: Asama Chemical Co., Ltd., Tokyo (JP); Combi Corporation, Tokyo (JP)

( * ) Notice: Subject to any disclaimer, the term of this patent is extended or adjusted under 35 U.S.C. 154(b) by 0 days.

(21) Appl. No.: 10/655,567

(22) Filed: Sep. 4, 2003

(65) Prior Publication Data

US 2004/0105851 A1 Jun. 3, 2004

(30) Foreign Application Priority Data

Sep. 5, 2002 (JP) ............... 2002-259766

(51) Int. Cl.
- *A61K 38/44* (2006.01)
- *A61K 47/42* (2006.01)
- *C12N 9/02* (2006.01)
- *C12N 9/96* (2006.01)

(52) U.S. Cl. .................. 424/94.4; 424/94.3; 435/189; 435/188

(58) Field of Classification Search ............ 424/94.4, 424/94.3, 94.1; 435/188, 189
See application file for complete search history.

(56) References Cited

U.S. PATENT DOCUMENTS 5,616,323 A * 4/1997 Ginoux et al. ............ 424/758
6,045,809 A 4/2000 Postaire et al.

OTHER PUBLICATIONS

Murcia et al., "Evaluation of the antioxidant properties of Mediterranean and tropical fruits compared with common food additives," J Food Prot 64(12):2037-2046, 2001.*
Takenaga et al., "Effect of lecithinized superoxide dismutase (PC-SOD) on experimental pulmonary metastasis in mice," Free Radic Biol Med 26(9-10):1117-1125, 1999.*
van Rossen et al., "Scavenging of reactive oxygen species leads to diminished peritoneal tumor recurrence," J Cancer Res 60:5625-5629, 2000.*
Das et al., "Inhibition of tumor growth and inflammation by consumption of tea," Phytother Res 16 (Suppl 1):S40-44, Mar. 26, 2002.*
Gorman et al., "The hope and the hype," Time 151(19):40-44, 1998, see also enclosed HTML copy, reference pp. 1-9.*
Gura, "Systems for identifying new drugs are often faulty," Science 278:1041-1042, 1997.*
Oxidants, antioxidants, and the degenerative diseases of aging by Bruce Ames et al, *Proc. Natl. Acad. Sci. USA*, vol. 90, pp. 7915-7922, Sep. 1993.
Malignant progression of a mouse fibrosarcoma by host cells reactive to a foreign body (gelatin sponge), by F. Okada et al, *Br. J. Cancer*, (1992), 66, 635-639.

* cited by examiner

*Primary Examiner*—Jon Weber
*Assistant Examiner*—Rosanne Kosson
(74) *Attorney, Agent, or Firm*—Flynn, Thiel, Boutell & Tanis, P.C.

(57) ABSTRACT

The invention prevents or treats a tumor, inhibiting tumor growth and malignant progression by providing an antitumor agent containing a treated SOD as the active ingredient, especially a melon SOD coated with gliadin. The invention also applies to a method of preventing or treating the tumor.

4 Claims, 1 Drawing Sheet

ANTI-TUMOR AGENT

This application claims priority to Japanese Application No. 2002-259766, filed on Sep. 5, 2002.

FIELD OF THE INVENTION

The present invention relates to an anti-tumor agent.

BACKGROUND OF THE INVENTION

The human body is made of 60 trillion cells. Cancer is a pathological state that threatens an individual's life by the cells being genetically changed and obtaining a potency of uncontrolled autonomous growth. A process of the development of cancer cells from normal cells have been elucidated by experiments on chemical carcinogenesis and it has been found that tumor development occurs as the result of the accumulation of genetic alterations.

From a standpoint of cell biological study of cellular alteration, the process of carcinogenesis is discussed as different stages of genetic alterations, i.e., initiation, promotion and progression. Initiation is a process in which a fixed change in a DNA sequence is given in a target cell. Promotion is a process in which the growth of an initiated target cell is selectively affected by various factors. However, the target cell still remains at a stage of a benign tumor. Progression is a process in which a conversion of a benign tumor cell into a malignant one proceeds by an acquisition of genetic changes which enable the tumor cell to exhibit more aggressive properties manifested by rapid growth, invasiveness and metastatic ability.

It is known that genetic changes are provoked by chemical carcinogens, radiation and reactive oxygens. Among them, reactive oxygens produced by inflammatory cells such as neutrophils may be a primary factor in the development of up to one-third of all cancer cells (Ames et al, Proc. Natl. Acad. Sci. USA 90; 7915–7922 1993).

Reactive oxygen species have long been suspect as agents which induce a genetic mutation. Reactive oxygen species include superoxides ($O_2^-$), hydrogen-peroxide ($H_2O_2$), hydroxy radicals ($OH^-$) and singlet oxygen ($^1O_2$). About 1 to 3% of oxygen inspired into the body by respiration becomes reactive oxygen during reduction to water. Reactive oxygen species have a potent oxidative activity and they are toxic to life. Therefore, nature developed by evolution a system which scavenges reactive oxygen for the purpose of detoxication of reactive oxygen by inducing/absorbing scavenging enzymes/antioxidants. Accordingly, as far as in the range of normal respiration, reactive oxygens generated may be detoxicated. However, various damages will occur when the amount of generated reactive oxygen exceeds the amount of detoxication capacity of reactive oxygen. Generation of reactive oxygens takes place at a site of inflammation in the body. Activated leucocytes and other phagocytic cells continuously produce vast amounts of reactive oxygen which cleave and modify DNA, oxidize lipids and sugars, denature proteins and inactivate enzymes resulting in damage to DNA and biomembranes. The present inventors developed an animal model which evaluates the effects of reactive oxygen to progression of cancer cells (Okada, F. et al, Br J Cancer. 66:635–639 1992).

The present inventors established a tumor cell clone (BMT-11cl-9) by cloning from a tumor developed by subcutaneous injection of a chemical carcinogen, methylcholanthrene, in a C57BL/6 mouse. BMT-11cl-9 cells were exposed in vitro to quercetin, a mutagen, at a concentration of 55 µm and several number of cloned cell lines were established. QR-32 cell line was one of them. QR-32 tumor cells do not grow in syngeneic C57BL/c mice when limited numbers of cells are injected intravenously or subcutaneously. However, a lethal growth occurs when QR-32 tumor cells are injected in immuno-suppressed mice. Accordingly it was found that QR-32 cell line was tumorigenic and that QR-32 was equivalent to a dormant tumor or a benign tumor. However, those tumor cells grew and formed a tumor mass when co-transplanted with a gelatin sponge. Then, the tumor mass was excised and a tumor cell suspension was made to establish culture cell lines from the tumor. Subcutaneous transplantation of the cells of these cell lines made a tumor mass at the injection site and intravenous injection of the cells of these cell lines produced lung metastasis. The results showed that the cells of the original QR-32 cell line which was not able to grow in vivo changed to be more malignant by co-implantation of the original cells with gelatin as shown by tumorgenicity and metastatic malignancy of these cell lines. As for mechanisms of malignancy, it was thought that because the gelatin-sponge was foreign to mice, inflammatory cells such as polymorpholeucocytes accumulated at the site of gelatin-sponge insertion and generated reactive oxygens. The reactive oxygens induced DNA mutation resulting in accomplishing malignant transformation of benign tumor cell line QR-32.

As for methods of treatment of tumors, there are surgical therapy, radiation therapy, chemotherapy and immunotherapy. The practice of cancer treatment is conducted by one of/or combining these treatment methods. Tumor masses which can be resected surgically are, as a general rule, treated by surgical operation. Tumor masses which cannot be treated by surgical operation, however, are treated by one or combinations of the other therapy methods except surgery. By the way, it is thought that progression of tumor cells, such as the loss of hormone-dependency (prostate tumor, breast tumor), acquisition of resistance to anti-tumor agents, metastatic ability and more rapid growth rate occur during the process of cancer treatment. Therefore, it is important to obstruct malignant transformation of tumor cells which occur during the process of cancer treatment for the purpose of successful tumor therapy.

Superoxide dismutase (hereinafter referred to as SOD) is an antioxidant enzyme that catalyzes the conversion of a super-oxide to hydrogen peroxide and is known as the enzyme that plays a central role in protecting from oxidative damages. Postarie and Eric invented a preparation of SOD molecules coated with lipids or proteins (hereinafter referred to as coated SOD preparation). They found that oral or parenteral administration of the preparation to animals elevated activity of SOD in the body compared with a preparation of SOD alone (U.S. Pat. No. 6,045,809).

SUMMARY OF THE INVENTION

There is no prior information concerning a method for obstructing the progression of tumors by the elimination of reactive oxygens.

The invention provides a method of preventing or treating tumors, which comprises administering a pharmacologically effective amount of a treated SOD to a patient suffering from a tumor.

It is preferred that the treated SOD is an SOD treated with a protein or lipid. The treated SOD is a SOD combined with gliadin, a melon SOD combined with gliadin or a melon SOD coated with gliadin.

In the invention, the treated SOD disclosed in U.S. Pat. No. 6,045,809 may be used, and the disclosure of this patent is hereby incorporated by reference thereto.

The treated SOD used in the present invention may be administered orally or parenterally.

The invention provides the use of the treated SOD for manufacturing an anti-tumor agent.

It is preferable that the coated SOD is a melon SOD coated with gliadin.

The present invention is based on the finding that a preparation of gliadin-coated, melon-derived SOD was tested for the inhibitory activity of tumor growth and malignant progression by using the inflammatory cell mediated progression model in mice and found that SOD-G inhibited tumor growth and malignant progression. Accordingly, the present invention for a new method of tumor prevention and treatment could be invented. The SOD treated with gliadin is hereinafter referred to as SOD-G.

The present invention also discloses a method of producing a composition for the prevention of tumor cell progression.

DETAILED DESCRIPTION OF INVENTION

Figure 1:
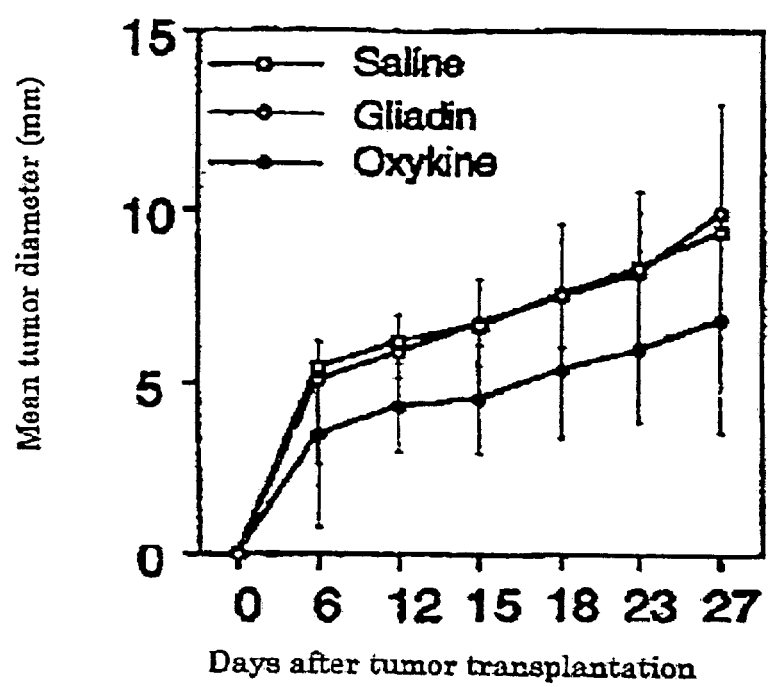
FIG. 1 shows tumor growth inhibitory effect of Oxykine in the Example.

It is preferable to use gliadin to coat SOD for producing SOD-G.

The anti-tumor agent of the present invention is used parenterally, as well as by the oral route.

Preparations containing the treated SOD of the present invention are used in the form of a powder, solid and suspension which in no way should be construed as being limited thereto. Tumor therapy, cancer prevention and therapy by the treated SOD can be widely used as a medicine, as well as a food.

The oral daily dose for humans is 10 to 1000 IU per man per day by one to three times dividedly.

The kinds of tumor for treatment by the present invention are brain tumors, laryngeal tumors, upper jaw tumors, pharyngeal tumors, lung tumors, esophagus tumors, colon tumors, liver tumors, gastric tumors, gall-bladder tumors, pancreas tumors, skin tumors, mammary tumors, uterus tumors, ovarian tumors, prostate tumors, kidney tumors, bladder tumors, goiters, multiple myelomas, lymphatic tumors, acute myelocytic leukemia and chronic myelocytic leukemia, but in no way should be construed as limiting the invention thereto.

The treated SOD of the present invention can be made according to the following production example.

PRODUCTION EXAMPLE 200 ml of 80% ethanol in a beaker is heated to 40° C. Then, 1.7 g of sorbitol, 0.75 g of glycerol, 5 g of gliadin and a 200 ml solution containing 10 mg/ml of melon SOD were added thereto in this order. The mixture was heated and stirred to obtain a clear solution. The solution was poured onto a glass plate and heated at 37° C. for 48 hours at a humidity of 2% to dry the solution. A dried film thus obtained was pulverized by using a pulverizer. Then, dextrin was added so as to make a powder of 2% SOD content.

EXAMPLE

Anti-tumor Activity of SOD-G

C57BL/6 female mice of 2 to 4 months old were used. The mice were housed and used for experimentation under a specific pathogen-free condition.

Cell culture: Tumor cells were cultured in a MEM medium containing 8% of fetal calf serum, pyruvate, non-essential amino-acids and L-glutamine at 37° C. in 95% air and 5% $CO_2$.

Insertion of gelatin sponge and tumor transplantation: Mice were anesthetized with ether and swabbed with 70% ethanol on the back and then a 10 mm incision was made in the right flank skin at the pelvic region. The mice had a piece of gelatin sponge (10×5×3 mm) surgically inserted into the subcutaneous pocket at the place of the incision. After closing the incision with a clip, 0.1 ml of tumor cell suspension containing $1 \times 10^5$ cells was injected into the site of gelatin sponge insertion. Measurement of tumor growth after inoculation was performed twice per week.

Medication of SOD-G: A preparation of SOD-G used in the study contained 1000IU SOD activity per g of preparation (trade name: Oxykine). As controls, groups of mice treated with physiological saline solution and also treated with gliadin were prepared. SOD-G was administered to the mice at an oral daily dose of 10 mg/kg of body weight/10 ml of saline from day $-2^{nd}$ to the $27^{th}$, making the transplant day the zero day. Each group consisted of 7 to 9 mice.

Result 1. Inhibition of Tumor Growth.

Effect of SOD-G on growth of tumor transplanted simultaneously with gelatin sponge was shown in Table 1, Experiment A.

The average growth curve of the SOD-G treated group was compared with those of saline and gliadin. As shown in FIG. 1, tumor growth was suppressed in the SOD-G treated group (FIG. 1).

As for rates of tumor take, those of the saline group and gliadin treated group were 8/9 and 8/8, respectively. On the other hand, that of the SOD-G treated group was 4/7, showing a suppressive effect but statistically not significant.

Result 2. Metastatic Potential of Growing Tumor.

In order to investigate whether the tumor cells which grew by simultaneous transplantation with gelatin sponge acquired malignancy by progression, each tumor nodule was surgically extracted on day 27 of the transplantation, and tumor cell culture lines were established from the individually developed tumors. The tumor cells of each line were cultured to eliminate host inflammatory cells and experiments which examined metastatic potential were conducted. $1 \times 10^6$ tumor cells of each tumor line were injected into 3 to 5 mice in the tail vein of normal syngeneic mice. The mice were killed on day 25 after implantation, and lungs and other organs were examined macroscopically for metastatic tumor nodules and incidences of lung metastasis were compared with that of the original tumor cell line, QR32, i.e., 0/10.

The result was as shown in Table 1, Experiment B, the rate of progression in the SOD-G treated group was 1/7. Comparing this datum with that of the saline group, 8/9, it can be concluded that a significant reduction in progression was observed.

Table 1 shows that SOD-G (Oxykine, tradename) prevented tumor growth and progression.

TABLE 1

Effects of SOD-G(Oxykine) on inflammation-promoted QR-32 mouse fibrosarcoma cell progression

| Experiment A: Tumorgenicity of QR-32 cells in mice treated with oxykine or gliadin | | Experiment B: Characteristics of the arising tumor lines | | | | | | | |
|---|---|---|---|---|---|---|---|---|---|
| | | | Lung-colonizing ability | | | Other organs with metastasis | | | |
| $1 \times 10^5$ of QR-32 cells were co-implanted with gelatin sponge into mice which had been administered with | Incidence (No. of mice with tumor take/no. of mice tested) | Cell lines established from the arising tumor | Incidence (No. of mice with lung metastasis/no. of mice tested) | p vs QR-32 | No. of lung metastatic nodules | Incidence (No. of mice with metastasis/no. of mice tested) | Sites (incidence) | Acquisition of metastatic phenotype | Rate of progression |
| — | — | QR-32 | 0/10 | | 0, 0, 0, 0, 0, 0, 0, 0, 0, 0 | 0/10 | No metastasis | – | — |
| Saline | 8/9 | QRsP-1 | 3/3 | p < 0.005 | 1, 3, 14 | 0/3 | No metastasis | + | 8/9 |
| | | QRsP-2 | 3/3 | p < 0.005 | 8, 13, 20 | 0/3 | No metastasis | + | |
| | | QRsP-3 | 4/4 | p < 0.001 | 3, 8, 14, >150 | 1/4 | Ovary(1/4) | + | |
| | | QRsP-4 | 3/4 | p < 0.05 | 0, 1, 3, 35 | 0/4 | No metastasis | + | |
| | | QRsP-6 | 3/5 | p < 0.05 | 0, 0, 2, 7, 8 | 1/5 | Ovary(1/5) | + | |
| | | Total | 16/19 | | | 2/19 | | 5/5 | |
| SOD-G | 4/7 | QRsP/SOD-G-1 | 0/4 | Ns | 0, 0, 0, 0 | 0/4 | No metastasis | – | 1/7 |
| | | QRsP/SOD-G-2 | 3/4 | p < 0.05 | 0, 2, 3, 18 | 0/4 | No metastasis | + | p < 0.05 |
| | | QRsP/SOD-G-3 | 2/4 | Ns | 0, 0, 5, 7 | 0/4 | No metastasis | – | vs |
| | | Total | 5/12 | | | 0/12 | | 1/3 | saline |
| Gliadin | 8/8 | QRsP/Glia-1 | 4/4 | p < 0.005 | 2, 2, 4, 1, 7 | 0/4 | No metastasis | + | 5/6 |
| | | QRsP/Glia-2 | 4/4 | p < 0.005 | 5, 6, 12, 14 | 0/4 | No metastasis | + | |
| | | QRsP/Glia-3 | 2/4 | Ns | 0, 0, 3, 8 | 0/4 | No metastasis | – | |
| | | QRsP/Glia-4 | 3/4 | p < 0.05 | 0, 5, 7, 22 | 1/4 | Ovary(1/4) | + | |
| | | QRsP/Glia-5 | 3/4 | p < 0.05 | 0, 2, 6, 12 | 0/4 | No metastasis | + | |
| | | QRsP/Glia-6 | 4/4 | p < 0.005 | 2, 5, 6, 7 | 1/4 | Ovary(1/4), Ascites(1/4) | + | |
| | | Total | 20/24 | | | 2/24 | | 5/6 | |

Clinical Trials

Clinical Studies Judged Effective through the use of SOD-G

Patient A. K. was a 72 year old man and was diagnosed with colon cancer three years before and the tumor was surgically removed. One liver metastatic nodule of 2 cm of diameter was discovered by CT scan by the inspection two years after the operation. Since the patient did not wish an operation or chemotherapy, Oxykine daily dose of 500 mg was administered once per day, and progress was observed. The tumor marker CEA at the time of an Oxykine recipe start was 16. After 6 months use of Oxykine, the CEA value was reduced to 6.8, and the size of the liver metastases remained at 2 cm diameter.

It was judged from the reduction of the CEA value and no growth of liver metastatic nodule that Oxykine took effect.

Patient S. T. was a 69 year old man. The man was diagnosed with prostate cancer five years before and radical cure-prostate gland surgery was performed. Although the prostate gland marker SPA value before an operation was 26, the value dropped to 0.1 after the operation and the normal value was maintained by two inspections in after years. In an inspection one year ago, the SPA value rose to 6.5, although it could not discover any tumor by CT scan, but it started the internal secretion chemotherapy (Leuprin+UFT). The SPA value three months after medical treatment was 7.5 Because the expected effect of medical treatment was not obtained, Oxykine at a daily dose of 300 mg was added to the treatment. SPA value 6 months after commencement of Oxykine treatment was 6.5. It was judged that Oxykine suppressed tumor growth because SPA value remained under a controlled tendency.

What is claimed is:

1. A method of inhibiting the change of a tumor in a subject from a dormant tumor or a benign tumor to a malignant tumor, comprising the step of administering to the subject in which the malignant progression is to be inhibited a pharmacologically effective amount of a superoxide dismutase coated with gliadin.

2. The method of claim 1, wherein the superoxide dismutase is a melon superoxide dismutase.

3. The method of claim 1, wherein the superoxide dismutase coated with gliadin is administered orally.

4. The method of claim 1, wherein the tumor is a colon tumor.

* * * * *